(12) United States Patent
Owsley et al.

(10) Patent No.: US 6,519,862 B1
(45) Date of Patent: Feb. 18, 2003

(54) DEVICE FOR THE ACQUISITION OF CONTOURED HUMAN BODY SURFACE VIBRATION SIGNALS

(75) Inventors: Norman L. Owsley, Gales Ferry, CT (US); Andrew J. Hull, Newport, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 77 days.

(21) Appl. No.: 09/678,897

(22) Filed: Oct. 4, 2000

(51) Int. Cl.⁷ ............................. A61B 1/00; G01B 3/00
(52) U.S. Cl. ................. 33/512; 33/501.02; 33/511; 33/552
(58) Field of Search ................ 33/501.02, 501.03, 33/501.04, 511, 512, 514.2, 515, 546, 551, 552, 555, 561.1

(56) References Cited

U.S. PATENT DOCUMENTS

| | | | |
|---|---|---|---|
| 3,945,122 A | * 3/1976 | Durand et al. | ................. 33/512 |
| 5,143,088 A | * 9/1992 | Marras et al. | ................. 33/512 |
| 5,375,610 A | * 12/1994 | LaCourse et al. | ............. 33/512 |
| 5,383,457 A | * 1/1995 | Cohen | ........................ 600/443 |
| 5,687,487 A | * 11/1997 | Johnson | ................... 33/501.02 |
| 5,761,005 A | * 6/1998 | McKay et al. | ........... 360/234.6 |
| 6,229,297 B1 | * 5/2001 | Bohn | ....................... 33/501.02 |
| 6,289,599 B1 | * 9/2001 | Leifeld et al. | ........... 33/501.02 |
| 6,295,737 B2 | * 10/2001 | Patton et al. | .................. 33/511 |

* cited by examiner

Primary Examiner—Diego Gutierrez
Assistant Examiner—Yaritza Guadalupe
(74) Attorney, Agent, or Firm—Michael J. McGowan; James M. Kasischke; Michael F. Oglo

(57) ABSTRACT

In accordance with the present invention, a device for acquiring contoured human body surface vibration signals is provided. The device comprises a first component for sensing the displacements of a skin surface as a function of time at multiple points on the human body, with the first component having a plurality of sensing elements, a second component for measuring time average displacements of the skin surface at nominal locations of the sensing elements in the first component; and a third component for correcting for the effect of positional error from a set of nominal displacement sensor locations.

6 Claims, 3 Drawing Sheets

DEVICE FOR THE ACQUISITION OF CONTOURED HUMAN BODY SURFACE VIBRATION SIGNALS

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION (1) Field of the Invention

The present invention relates to a device and a method for the acquisition of contoured human body surface vibration signals.

(2) Description of the Prior Art

Devices are known in the prior art to detect the contour of shapes. Some of these devices are illustrated in U.S. Pat. No. 4,700,487 to Bogle; U.S. Pat. No. 4,956,924 to Hu; and U.S. Pat. No. 5,546,668 to Ahdoot.

U.S. Pat. No. 5,257,184 to Mushabac illustrates a device for providing a computer with electrically encoded data specifying curvilinear contours of an object. The device comprises a manipulable frame member, componentry for establishing a reference position, a plurality of stylus elements, and means for measuring displacements of the stylus elements along respective axes. The componentry for establishing a reference position includes circuits transmitting an electrical signal encoding a location of a reference point on the frame member to the computer. The stylus elements are each slidably mounted to the frame member for motion along respective axes extending at least partially parallel to one another. The means for measuring or detecting stylus displacements is operatively connected to the stylus elements for transmitting to the computer electrical signals encoding displacements of the stylii along the respective axes. The Mushabac device may be used to determine the contour of a human tooth.

U.S. Pat. No. 5,957,868 to Case et al. illustrate a surface contour measurement instrument in which back-to-back hydraulically linked pistons are mechanically coupled to contact probes and measurement sensors. The pistons are hydraulically linked by small diameter flexible conduits which enable the contact probes and the measurement sensors to be mounted and moved independently of each other without affecting the ability of the measurement instrument to simultaneously measure a plurality of points on a selected predefined surface, such as a human tooth.

SUMMARY OF THE INVENTION

It is a principal object of the present invention to provide a device for the acquisition of contoured human body surface vibration signals.

In accordance with the present invention, a device and a method for acquiring contoured human body surface vibration signals is provided. A flexible array of sensing elements is used to measure displacements of a skin surface as a function of time at multiple points on the human body. A contour estimation component is used to measure the time average displacements of the skin surface at nominal locations of the sensing elements in the flexible array. A computer is used to correct the effect of positional error determined by the contour estimation component from a set of data gathered by the flexible array.

Other details of the device of the present invention, as well as other objects and advantages attendant thereto, are set forth in the following detailed description and the accompanying drawings, wherein like reference numerals depict like elements.

DESCRIPTION OF THE PREFERRED EMBODIMENT(S)

Figure 1:
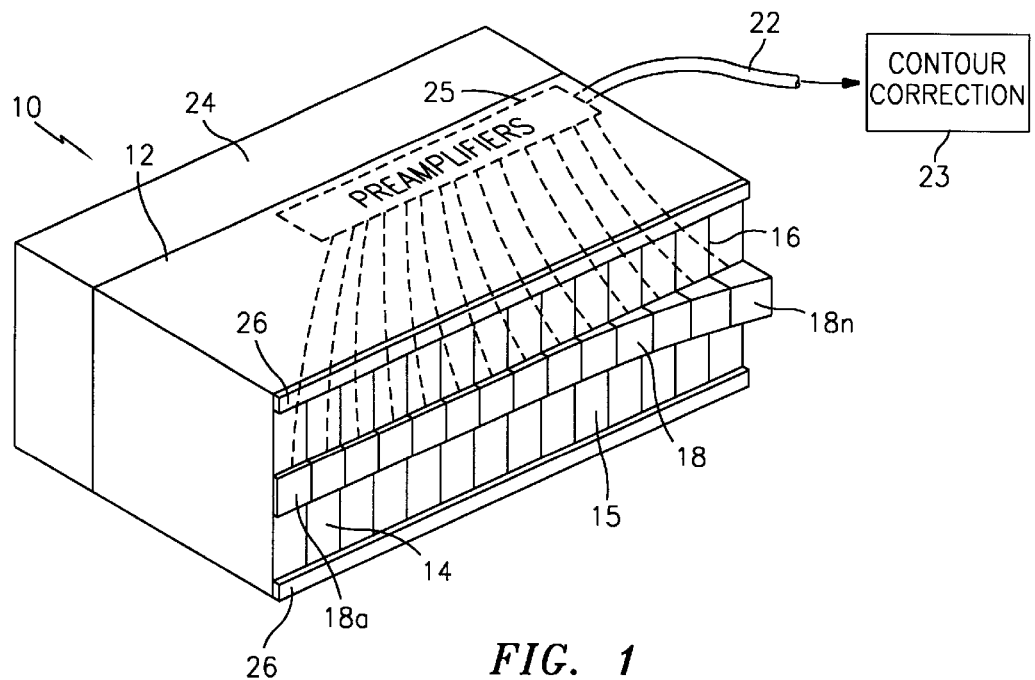
FIG. 1 is a perspective view of a first embodiment of a fixed contour, flexible array component used in the device of the present invention.

The device for acquiring contoured human body surface vibration signals in accordance with the present invention has three components. The first component is a fixed contour, flexible array component 10, see FIG. 1, containing multiple transducer elements 14 for sensing vibrational displacements of the skin surface at multiple points on the human body. The flexible array component 10 is such that the contoured surface of the body causes individual displacement sensors 14 in the array aperture conforming to the exact variation of the surface topology and producing electrical signals with amplitude in proportion to the magnitude of the time varying displacements about some zero displacement, time averaged reference. The individual sensors 14 have sufficient positional flexibility in a direction perpendicular to the body surface at the sensor 14 to allow the array to conform to an irregular surface and maintain the required level of displacement signal produced by each displacement sensor.

The second component of the device is a mechanical body surface contour estimation component 30 for measuring the displacements of the skin at the nominal locations of the elements in the flexible array. The contour estimation component 30 estimates and records the locations of the individual displacement sensors in the flexible array component by, first, positioning individual mechanical skin contacts and, second, securing such contacts to record the contact time averaged position.

The third component of the device comprises a contour correction component 23. This can be a computer or other device having a signal processing function that converts the estimated contour shape provided by the contour estimation component 30 into a table of spatial location correction factors required for the analysis of the acquired displacement sensor output signal data. In the contour correction component 23, the estimated surface contour geometry is then used in the correction of either time delay or, equivalently, phases shifts at individual frequency estimates used in an imaging process involving the time delay alignment and weight summation of space and time sample points on a propagating shear wave vibration front emanating from an assumed focal point inside the body.

Referring now to FIG. 1, an embodiment of a flexible array component 10 is illustrated. As shown therein, the flexible array component 10 has a single rigid chassis 12 which provides a stable mechanical frame and a relative spatial coordinate system frame of geometric reference for the individual displacement sensors 14 relative to chassis 12. The individual displacement sensors 14 are such they can be attached securely to the mechanical frame provided by the chassis 12 at either one or two points, as disclosed below.

The individual displacement sensors 14 are preferably piezoelectric strain gauge displacement sensors. In this embodiment, sensor 14 is a flexible band 15 with a standoff foot 18 joined thereto. Flexible band 15 is fixed at each end to chassis 12. A standoff foot 18 is fixed to the intermediate portion of band 15.

In order to maintain piezoelectric flexible bands 15, at optimum efficiency, bands 15 must operate with a low strain. This strain would be exceeded if the flexible array component were positioned on a chest with the bands 15 accommodating all of the variation of different chests. In the first embodiment, this variation is accommodated by thickening those feet 18 that will be positioned on a region of the chest further away from chassis 12. The thicknesses of the feet 18 can be provided as a fixed default body surface contour, as an individually tailored contour, or as one of a set of contours determined by measurement. The thickness of each foot is a known quantity and can be incorporated in calculations that depend on the positioning of the sensor relative to the chest. As an alternative embodiment, the flexible array component 10 can have the nominal body surface contour machined into the lower edge of chassis 12. This lower chassis contour would permit the use of feet 18 which are all the same height.

The rigid frame 10 contains the electrical leads carrying the signal from each displacement sensor 14. The electrical leads are coalesced into a single flexible cable bundle 22 attaching the leads to contour correction and recording electronics 23 for acquisition of the output of the individual sensors 14. In a preferred construction of the array, an enclosure 24 is provided which houses electronic preamplifiers 25 for the strain gauge transducer output signals. The electronic preamplifiers 25 can comprise any suitable preamplification means known in the art and should be located as physically close to the sensors 14 as possible. The chassis 12 and the enclosure 24 may be formed as an integral unit if desired.

The sensors 14 need to be electrically isolated from the body skin surface 20 because skin 20 may cause both electrical short circuiting and electromagnetic interference. This isolation can be accomplished with rubber strips 26 adhesively joined to chassis 12. The strips 26 physically separate the sensors 14 from the skin and allow only the feet 18 to contact the skin surface 20.

Figure 2:
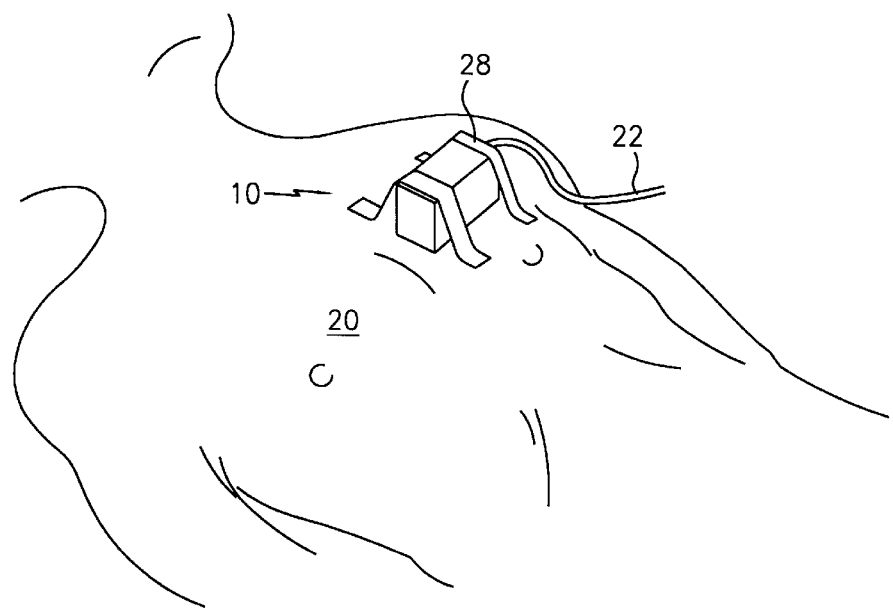
FIG. 2 illustrates the component of FIG. 1 placed on a human body.

As shown in FIG. 2, the flexible array component 10 may be stabilized on the body surface 20 using a light medical single-sided adhesive tape 28.

Figure 5:
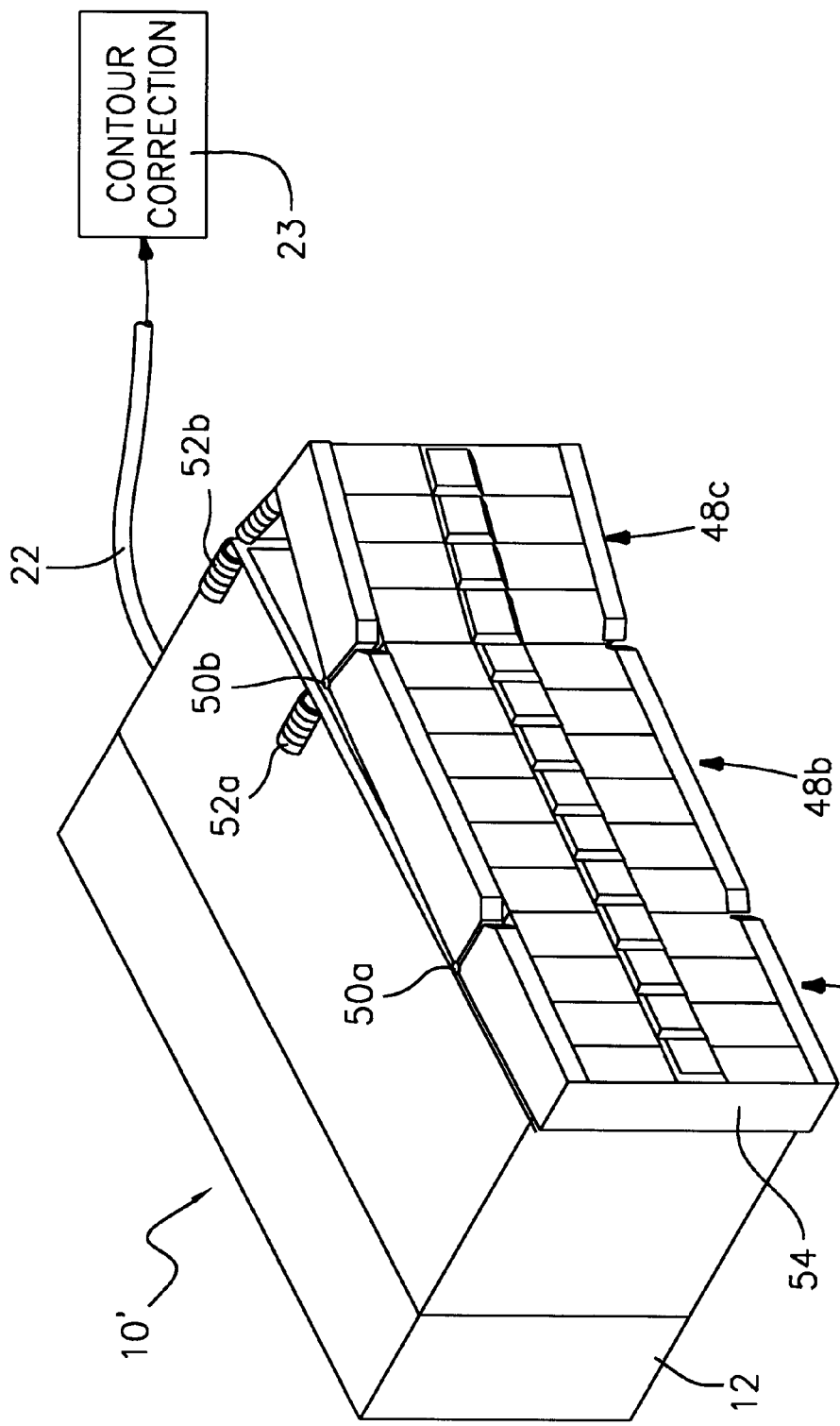
FIG. 5 illustrates an alternative embodiment of a conformable array component wherein the body curvature is accounted for in the shape of a replaceable head unit.

As shown in FIG. 5, an alternative embodiment of a flexible array component 101 can conform to the contoured body surface by constructing the flexible array component chassis 12 in either two or more subchassis 48 which are hinged 50 together. The maximum angle between the units would be constrained so that the internal amplifier electronics could remain rigidly affixed at points only in one subchassis 48a. The position of the hinged chassis units 48b and 48c is fixed with thumb dialed adjustment screws 52a and 52b. A capability for a protractor type angle setting between subchassis would be provided after the flexible array component is located on the body and secured in the contoured configuration with easily enabled set screws or a functional equivalent. The entire multiple head unit 54 could be replaceable.

Figure 4:
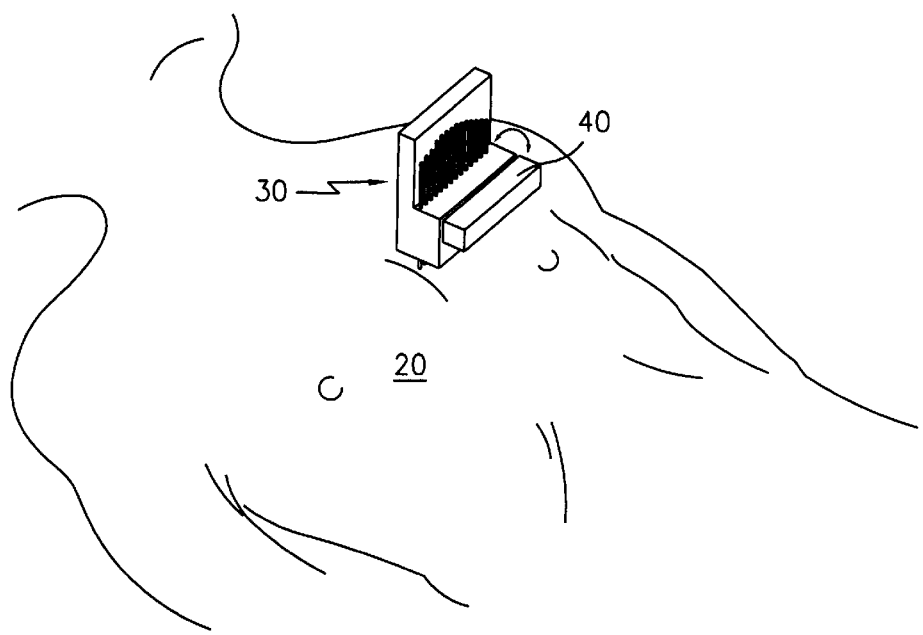
FIG. 4 illustrates the component of FIG. 3 placed on a human body.

One embodiment of the contour estimation component 30 is illustrated in FIG. 4. As shown therein, the contour estimation component 30 includes a rigid frame 31 that contains multiple equal length mechanical members 32, such as pins, cylinders, wire segments, and the like, that slide easily through holes 34 that are located in the same relative positions in the lower surface of the frame 30 as the geometric centers of feet 18 in the flexible array component 10. With the body surface 20 for which the contour is to be estimated oriented nominally in the horizontal plane below component 30, members 32 are free to slide up and down vertically with gravity such that each member 32 makes light contact with the skin surface 20 below hole 34.

Figure 3:
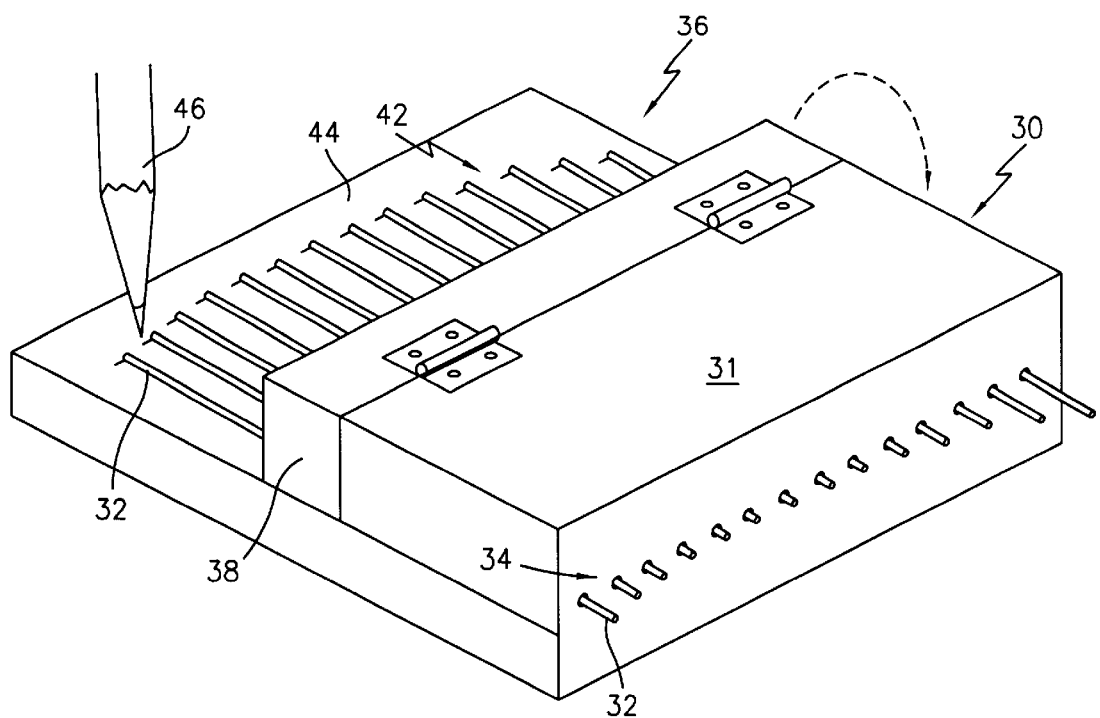
FIG. 3 is a perspective view of a mechanical body surface contour estimation component used in the device of the present invention.

The contour estimation component 30 is provided with a pin capture mechanism 36 for retaining the positions of members 32 at the position where each member 32 contacts the skin surface 20. The points of contact conform to the surface contour under the holes 34. As shown in FIGS. 3 and 4, this pin capture mechanism 36 comprises a hinged cover 38 with a surface 40 that, when swung into the capture position, holds the members 32 in the contour record position when the contour estimation component 30 is removed from the body surface 20. Surface 40 can be soft, spongy rubber or some other retaining material.

Having stabilized the members 32 in the contour sensing configuration, a recording mechanism 42 which records the location of the tops of the members 32 and therefore, because the members 32 are of equal length, the sampled skin contour below the contour estimation component 30. The recording mechanism 42 can be as simple as a cardboard tab 44 which can slide in behind the tops of the members 32 and upon which a marking device 46 can be used to manually record the relative locations of the tops of all the members 32. The measured contour can then be transferred to the contour correction component 23 by manual entry. Other embodiments of contour estimation component 30 could provide automatic transfer of measurements.

It is desirable to achieve a position location estimate at the surface of the body that is accurate to within a nominal 0.1 wavelength, $\lambda$, referenced to the wavelength of a shear wave propagating in the body and producing the vibrational excitation at the body surface. As an example of this accuracy objective, assume that the wave speed of a body shear wave at a frequency of f=400 Hz is c=6 meters/second. The desired positional accuracy is therefore=(0.1)$\lambda$=(0.1)(c/f)=0.15 cm.

In the spatial focusing image function, hereinafter referred to as focused beamforming, the contour correction component 50 concerns the electrical output of the nth of N displacement sensors 14 which is denoted as $x_n(t)$. In a preferred embodiment of the device of the present invention, N is equal to fourteen.

The contour correction component 50 has the function of inserting an approximation to the time required for energy emanating from a particular point internal to the body and which point is an element in a volume of such points wherein the energy distribution is to be estimated and recorded in the form of an image. Because body tissue is a dispersive medium in a range of frequency essential to the FB function, the wave speed is a function of the frequency of interest. As such, the contour correction component function is best performed in the frequency domain according to the principles of the Fourier F( ) transform relationship:

$$X_{n/CEC}(f)=F\{x_n(t-_n),f\}=X_n(f)\exp(-j2fd_n/c(f))$$

where $X_n(f)$ is the Fourier transform of the nth sensor output $x_n(t)$, $_n=d_n/c(f)$ is the time delay required to correct for the deviation of the actual contour measured by the CEC from the nominal contour at frequency f.

In operation, the contour correction component 23 comprises a processor which is programmed to carry out the various contour correction component functions. For example, the estimated contour shape recorded by the contour estimation component 30 is entered into the contour correction component. This can be done, for example, by scanning in the recording mechanism or manually entering the numbers, or automatically entering the numbers. Thereafter, the contour correction component 23 through its programming converts the estimated contour shape into a table of spatial location correction factors taken directly from the contour estimation correction member displacements, which table is stored in the processor.

As energy emanates from a particular point internally of the human body, it will cause the body skin surface 20 to move. The sensors 14 in the FAC 10 detect the movement of the body skin surface 20. The output of each of the sensors 14 is fed to the contour correction component 23.

As previously mentioned, the contour correction component 23 processes the output of each transducer and inserts a time delay factor to account for the time required for the energy emanating from the internal point to reach the surface of the skin at the location of the transducer including the contour estimation component measure correction$_n$. Using this information, it is possible to estimate the internal energy distribution and record it as an image. Details of this aspect are found in U.S. Pat. No. 5,727,561 which is hereby incorporated by reference herein.

It is apparent that there has been provided in accordance with the present invention a device for the acquisition of contoured human body surface vibration signals which fully satisfies the objects, means, and advantages set forth hereinbefore. While the device of the present invention has been described in the context of specific embodiments thereof, other variations, modifications, and alternatives will become apparent to those skilled in the art after reading the instant disclosure. Therefore, it is intended to embrace such variations, modifications, and alternatives which fall within the broad scope of the appended claims.

What is claimed is:

1. A device for the acquisition of contoured human body surface vibration signals which comprises:

a plurality of sensing elements providing displacements of a skin surface as a function of time at multiple points on the human body, wherein said sensing elements comprise transducers providing displacement signals corresponding to said provided displacement as a function of time;

a measuring means providing measuring time average displacements of the skin surface at nominal locations of said sensing elements;

a correcting means receiving the displacements as a function of time and said time average displacements and correcting said displacements as a function of time for said time average displacement;

a rigid chassis having said transducers mounted thereto for providing mechanical stability to said transducers; and a plurality of feet with each foot attached to one of said transducers.

2. The device according to claim 1, wherein each said foot has a thickness conforming with a default body surface contour.

3. A device for the acquisition of contoured human body surface vibration signals which comprises:

a rigid chassis;

a plurality of sensing elements providing displacements of a skin surface as a function of time at multiple points on the human body, wherein each said sensing element comprises a piezoelectric strain gauge displacement sensor mounted in two places to said rigid chassis providing displacement signals corresponding to said provided displacement as a function of time;

a measuring means providing measuring time average displacements of the skin surface at nominal locations of said sensing elements; and a correcting means receiving the displacements as a function of time and said time average displacements and correcting said displacements as a function of time for said time average displacement.

4. The device according to claim 3, further comprising electrical insulation means secured to said chassis to electrically isolate said sensing elements from the body skin surface.

5. The device according to claim 3 wherein said rigid chassis has a nominal body surface contour machined into a lower edge of the chassis.

6. The device according to claim 3, wherein said sensing elements are flexible so as to allow the sensing elements to deviate sightly from a nominal fixed contour.

* * * * *